United States Patent
Harandi et al.

(10) Patent No.: US 10,626,338 B2
(45) Date of Patent: Apr. 21, 2020

(54) EFFICIENT PROCESS FOR CONVERTING HEAVY OIL TO GASOLINE

(71) Applicant: ExxonMobil Research and Engineering Company, Annandale, NJ (US)

(72) Inventors: Mohsen N. Harandi, New Hope, PA (US); Suriyanarayanan Rajagopalan, Spring, TX (US)

(73) Assignee: EXXONMOBIL RESEARCH AND ENGINEERING COMPANY, Annadale, NJ (US)

( * ) Notice: Subject to any disclaimer, the term of this patent is extended or adjusted under 35 U.S.C. 154(b) by 0 days.

(21) Appl. No.: 15/825,214

(22) Filed: Nov. 29, 2017

(65) Prior Publication Data

US 2018/0171241 A1     Jun. 21, 2018

Related U.S. Application Data

(60) Provisional application No. 62/434,496, filed on Dec. 15, 2016.

(51) Int. Cl.
*C10G 2/00*     (2006.01)
*C10G 57/00*    (2006.01)
(Continued)

(52) U.S. Cl.
CPC ............... *C10G 57/00* (2013.01); *C07C 1/12* (2013.01); *C07C 1/20* (2013.01); *C07C 2/12* (2013.01); *C07C 2/864* (2013.01); *C07C 29/153* (2013.01); *C10B 55/10* (2013.01); *C10G 9/005* (2013.01); *C10G 9/32* (2013.01); *C10G 50/00* (2013.01); *C10G 57/02* (2013.01); *C10G 70/00* (2013.01); *C10J 3/463* (2013.01); *B01J 29/40* (2013.01);
(Continued)

(58) Field of Classification Search
None
See application file for complete search history.

(56) References Cited

U.S. PATENT DOCUMENTS 3,354,078 A    11/1967    Miale et al.
3,661,543 A     5/1972    Saxton
(Continued)

FOREIGN PATENT DOCUMENTS

WO    WO-2016205411 A2 *    12/2016    ............... C07C 2/82

OTHER PUBLICATIONS

Stöcker, M. "Methanol-to-hydrocarbons: catalytic materials and their behavior" Microporous and Mesoporous Materials 29 (1999) 3-48 (Year: 1999).*
(Continued)

*Primary Examiner* — Medhanit W Bahta
(74) *Attorney, Agent, or Firm* — Chad A. Guice; Hsin Lin

(57) ABSTRACT

Methods and systems are provided for making gasoline. The method includes converting a resid-containing feed to a first fuel gas and a fluid coke in a fluidized bed reactor; gasifying the fluid coke with steam and air to produce a second fuel gas, said second fuel gas comprising a syngas; contacting the first fuel gas with a first conversion catalyst under first effective conversion conditions to form an effluent comprising $C_5+$ hydrocarbon compounds; and converting the syngas to gasoline boiling range hydrocarbons by converting the syngas to a methanol intermediate product.

12 Claims, 1 Drawing Sheet

(51) Int. Cl.
*C10G 50/00* (2006.01)
*C10G 9/00* (2006.01)
*C10G 70/00* (2006.01)
*C10G 57/02* (2006.01)
*C10G 9/32* (2006.01)
*C10B 55/10* (2006.01)
*C10J 3/46* (2006.01)
*C07C 29/153* (2006.01)
*C07C 2/86* (2006.01)
*C07C 1/20* (2006.01)
*C07C 1/12* (2006.01)
*C07C 2/12* (2006.01)
*B01J 29/40* (2006.01)
*C07C 31/04* (2006.01)
*C07C 41/09* (2006.01)
*C07C 43/04* (2006.01)
*C08F 10/00* (2006.01)

(52) U.S. Cl.
CPC .......... *C01B 2203/02* (2013.01); *C07C 31/04* (2013.01); *C07C 41/09* (2013.01); *C07C 43/043* (2013.01); *C08F 10/00* (2013.01); *C10G 2300/708* (2013.01); *C10G 2400/02* (2013.01); *C10G 2400/20* (2013.01); *C10G 2400/22* (2013.01); *C10G 2400/26* (2013.01); *C10J 2300/0943* (2013.01); *C10J 2300/0956* (2013.01); *C10J 2300/0976* (2013.01); *C10J 2300/1665* (2013.01)

(56) References Cited

U.S. PATENT DOCUMENTS

| | | |
|---|---|---|
| 3,702,516 A | 11/1972 | Luckenbach |
| 3,702,886 A | 11/1972 | Argauer et al. |
| 3,709,979 A | 1/1973 | Chu |
| 3,759,676 A | 9/1973 | Lahn |
| 3,832,449 A | 8/1974 | Rosinski et al. |
| 3,894,102 A | 7/1975 | Chang et al. |
| 3,960,978 A | 6/1976 | Givens et al. |
| 4,016,218 A | 4/1977 | Haag et al. |
| 4,016,245 A | 4/1977 | Plank et al. |
| 4,046,859 A | 9/1977 | Plank et al. |
| 4,076,842 A | 2/1978 | Plank et al. |
| 4,104,151 A | 8/1978 | Rubin et al. |
| 4,213,848 A | 7/1980 | Saxton |
| 4,269,696 A | 5/1981 | Metrailer |
| 4,375,573 A | 3/1983 | Young |
| 4,397,827 A | 8/1983 | Chu |
| 4,417,000 A | 11/1983 | Slaugh et al. |
| 4,547,616 A | 10/1985 | Avidan et al. |
| 4,579,999 A | 4/1986 | Gould et al. |
| 4,751,338 A | 6/1988 | Tabak et al. |
| 4,810,357 A | 3/1989 | Chester et al. |
| 4,827,069 A | 5/1989 | Kushnerick et al. |
| 4,954,325 A | 9/1990 | Rubin et al. |
| 4,992,607 A | 2/1991 | Harandi et al. |
| 5,472,596 A | 12/1995 | Kerby et al. |
| 2009/0056225 A1 | 3/2009 | Schinski |
| 2012/0116141 A1* | 5/2012 | Godsmark ................ C07C 2/12 585/533 |
| 2015/0005207 A1* | 1/2015 | Milam ..................... C07C 1/20 507/257 |
| 2015/0368572 A1 | 12/2015 | Rajagopalan et al. |
| 2017/0137720 A1* | 5/2017 | Harandi ................... B01J 29/40 |

OTHER PUBLICATIONS

Helton, T. et al. GTL—Technology Forum 2014 "Methanol to Gasoline Technology, An Alternative for Liquid Fuel Production" Jul. 30-31, 2014 (Year: 2014).*

Weisz et al., "Superactive Crystalline Aluminosilicate Hydrocarbon Catalysts", Journal of Catalysis, 1965, pp. 527-529, vol. 4.

Miale et al., "Catalysis by Crystalline Aluminosilicates", Journal of Catalysis, 1966, pp. 278-287, vol. 6.

Olson et al., "Chemical and Physical Properties of the ZSM-5 Substituional Series", Journal of Catalysis, 1980, pp. 390-396, vol. 61.

Kamienski et al., "Coking Without the Coke", Hydrocarbon Engineering, Mar. 2008.

Zhao et al., "Coal to Clean Gasoline", Hydrocarbon Engineering, Mar. 2008.

The International Search Report and Written Opinion of PCT/US2017/063575 dated Feb. 21, 2018.

* cited by examiner

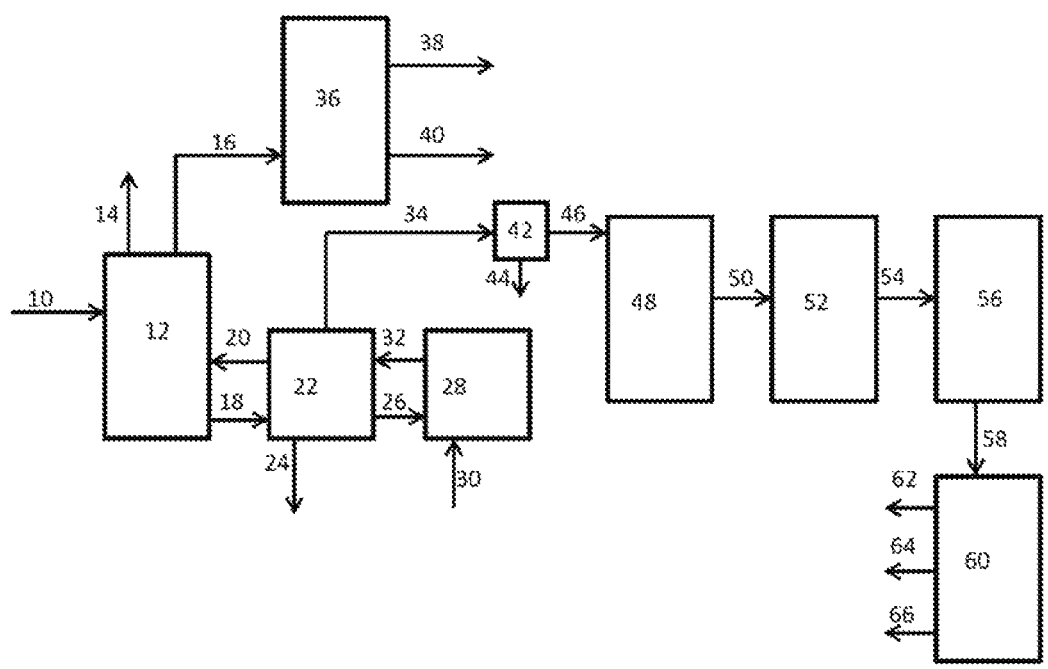

EFFICIENT PROCESS FOR CONVERTING HEAVY OIL TO GASOLINE

CROSS-REFERENCE TO RELATED APPLICATIONS

This application claims priority to U.S. Provisional Application Ser. No. 62/434,496 filed Dec. 15, 2016, which is herein incorporated by reference in its entirety.

FIELD

This application relates to the field of upgrading resid to gasoline.

BACKGROUND

Conventional heavy oil conversion processes, such as delayed coking and fluid coking produce coke or heavy products, that depending on feed quality, can be as much as 30-40 wt % of the feed processed by the conversion unit. The FLEXICOKING process, which is an on-catalytic thermal conversion procdess, is a continuous and self-contained fluidized bed integrated coking and gasification technology in which the fluid coke produced in the reactor is gasified with process steam and air to yield a higher value fuel gas.

In a conventional methanol-to-gasoline process, a mixture of methanol and dimethyl ether is fed along with a light hydrocarbon recycle gas into an axial-flow packed-bed reactor containing a catalyst to yield gasoline boiling range hydrocarbons and lighter hydrocarbons.

Such processes are generally not integrated in practice; however, in the present application it is shown that integration of the processes can achieve improved yields of higher value hydrocarbons while provided other process advantages.

SUMMARY

In one aspect, a method is provided for making gasoline. The method includes converting a resid-containing feed to a first fuel gas and a fluid coke in a fluidized bed reactor; gasifying the fluid coke with steam and air to produce a second fuel gas, said second fuel gas comprising a syngas; contacting the first fuel gas with a first conversion catalyst under first effective conversion conditions to form an effluent comprising C5+ hydrocarbon compounds, wherein the first effective conversion conditions comprise a pressure of less than about 300 psig (2.1 MPa) and a temperature of at least about 550° F. (288° C.); and converting the syngas to gasoline boiling range hydrocarbons by converting the syngas to a methanol intermediate product.

In another aspect, a system is provided for making gasoline. The system includes a fluidized bed reactor, the fluidized bed reactor receiving a resid-containing feed and operating under conditions suitable to convert the resid-containing feed to a first fuel gas and a fluid coke. The system also includes a gasifier, the gasifier receiving the fluid coke and combining the fluid coke with steam and air to produce a second fuel gas, said second fuel gas comprising a syngas. The system further includes a reactor, the reactor receiving (a) the first fuel gas and (b) the syngas or a methanol intermediate product made from the syngas, the reactor containing a first conversion catalyst and operating under first effective conversion conditions to form an effluent comprising C5+ hydrocarbon compounds, wherein the first effective conversion conditions comprise a pressure of less than about 300 psig (2.1 MPa) and a temperature of at least about 550° F. (288° C.).

DRAWINGS

The FIGURE is a schematic illustrating an exemplary process of converting resid to gasoline according to one or more embodiments of the present invention.

DETAILED DESCRIPTION

Systems and methods are provided for converting a resid-containing heavy oil feed to gasoline boiling range hydrocarbons. Advantageously, such conversion process may improve the yield of higher value hydrocarbon products, such as gasoline, while providing various process advantages such as improved efficiencies and the potential elimination of process equipment.

One or more of the foregoing advantages may be achieved by converting a resid feed to a first fuel gas and a fluid coke in a fluidized bed reactor; gasifying the fluid coke with steam and air to produce a second fuel gas, said second fuel gas comprising a syngas; contacting the first fuel gas with a conversion catalyst under effective conversion conditions to form an effluent comprising C5+ hydrocarbon compounds, wherein the effective conversion conditions comprise a pressure of less than about 300 psig (2.1 MPa) and a temperature of at least about 550° F. (288° C.); and converting the syngas to gasoline boiling range hydrocarbons by converting the syngas to a methanol intermediate product.

As used herein, and unless specified otherwise, "gasoline" or "gasoline boiling range hydrocarbons" refers to a composition containing at least predominantly C5-C12 hydrocarbons. In one embodiment, gasoline or gasoline boiling range components is further defined to refer to a composition containing at least predominantly C5-C12 hydrocarbons and further having a boiling range of from about 100° F. to about 450° F. In an alternative embodiment, gasoline or gasoline boiling range components is defined to refer to a composition containing at least predominantly C5-C12 hydrocarbons, having a boiling range of from about 100° F. to about 400° F., and further defined to meet ASTM standard D439.

An exemplary embodiment is illustrated in the FIGURE. A heavy oil feed 10 is supplied to reactor 12, which is fluidized-bed reactor operating under conditions suitable to thermally crack the heavy oil feed. Liquid reaction products 14, which include gas oils boiling between about 430 F and 950 F, and a fuel gas 16, which includes hydrocarbons boiling below about 430 F (thus, including naphtha boiling range hydrocarbons as well as C4 and lighter hydrocarbons), are effluents from reactor 12. The reactor 12 contains hot coke particles 20 which are provided by way of heater 22, which also preheats cold coke particles 18 from reactor 12. A portion of coke 24 is withdrawn continuously from the heater 22 to maintain the desired material balance of coke particles.

Preheated coke particles 26 from heater 22 are combined with process steam and air 30 in gasifier 28 and the gasified stream 32 is fed back to heater 22. A FLEXIGAS stream 34, which includes syngas and other gases, such as N2, are taken from heater 22 and fed to a separator 42, which may be a separation block, to yield a syngas stream 46. Nitrogen and other components are separated as stream 44.

Fuel gas stream 16 is fed to a reactor 36 containing a conversion catalyst and operating under conditions to oligomerize olefins in the fuel gas stream 16. In an exemplary embodiment, the fuel gas stream 16 contains mainly C2-, C3-, C4- or C5- hydrocarbons. Such oligomerization may be performed by utilizing a ZSM-5 catalyst, for example. Further description of such reaction conditions are described in greater detail subsequently. From the reactor 36, a gasoline stream 40 is obtained along with a stream of lighter hydrocarbons 38, which may include C4- hydrocarbons.

Syngas stream 46 may be fed to a methanol synthesis reactor 48 to produce a methanol containing effluent 50. The methanol containing effluent 50 may then be fed to a dimethyl ether reactor 52 where at least a portion of the methanol in the stream 50 is converted to dimethyl ether. Although reactor 48 and 52 are depicted as separate reactors, it should be noted that both reactions may be performed in the same reactor. The reactions performed in reactor(s) 48 and 50 are described in greater detail subsequently.

The effluent 54 of the reactor 52, which includes dimethyl ether and, optionally, some methanol may then be fed to reactor 56. In reactor 56, the dimethyl ether is contacted with a conversion catalyst and converted into gasoline boiling range hydrocarbons as well as C4's and lighter hydrocarbons. The reaction performed in reactor 56 is described in greater detail subsequently. The effluent 58 of the reactor 56 is sent to separation system 60, which can include multiple separation units such a deethanizer and a stabilizer, for separating a C2- hydrocarbon stream 62 and a light stream for example a propane stream 64, respectively. The remaining gasoline range hydrocarbons (e.g., C5+ hydrocarbons) may then be fed to gasoline blending pools where it is blended with other refinery gasoline streams, such as gasoline stream 40.

The FIGURE is intended to illustrate one possible configuration for a system for converting heavy oil to gasoline. Not all of the process units depicted in the FIGURE are essential, and some process units may be omitted. For example, in an exemplary embodiment, reactor 52 may be omitted and methanol is sent directly to reactor 56 for conversion. Further, in an exemplary embodiment, reactor 36 and reactor 56 may be one reaction zone upgrading both intermediate methanol and olefins in the first fuel gas stream.

Resid Containing Feedstocks

The processes and systems described herein have particular utility for heavy oils, such as resid-containing feedstocks. Various resid-containing feeds may be employed including atmospheric distillation resid, vacuum resid, catalytic cracker residual oils, hydrocracker residual oils, and residual oils from other refinery units. Such feedstocks typically consist of non-volatile, asphaltic and aromatic materials with "theoretical" boiling points exceeding 1000° F. at atmospheric pressure. The boiling points are "theoretical" because these materials may coke or crack from thermal decomposition before they reach such temperatures.

Feedstocks useful in the present process normally consist of refinery process streams which cannot economically be further distilled, catalytically cracked, or otherwise processed to make fuel-grade blend streams. Typically, these materials are not suitable for catalytic operations because of catalyst fouling and/or deactivation by ash and metals.

Heavy oils which may be processed by the fluid coking process include heavy atmospheric resids, petroleum vacuum distillation bottoms, aromatic extracts, asphalts, and bitumens from tar sands, tar pits and pitch lakes of Canada (Athabasca, Alta.), Trinidad, Southern California (La Brea (Los Angeles), McKittrick (Bakersfield, Calif.), Carpinteria (Santa Barbara County, Calif.), Lake Bermudez (Venezuela) and similar deposits such as those found in Texas, Peru, Iran, Russia and Poland.

Generating Fuel Gases with Fluidized Bed Reactor

Fluidized bed coking is a petroleum refining process in which heavy petroleum feeds, typically the non-distillable residues (resids) from the fractionation of heavy oils are converted to lighter, more useful products by thermal decomposition (coking) at elevated reaction temperatures, typically about 480 to 590° C., (about 900 to 1100° F.) and in most cases from 500 to 550° C. (about 930 to 1020° F.).

The process is carried out in a unit with a large reactor (e.g., reactor 12 of the FIGURE) containing hot coke particles which are maintained in the fluidized condition at the required reaction temperature with steam injected at the bottom of the vessel with the average direction of movement of the coke particles being downwards through the bed. The heavy oil feed is heated to a pumpable temperature, typically in the range of 350 to 400° C. (about 660 to 750° F.) mixed with atomizing steam, and fed through multiple feed nozzles arranged at several successive levels in the reactor. Steam is injected into a stripping section at the bottom of the reactor and passes upwards through the coke particles descending through the dense phase of the fluid bed in the main part of the reactor above the stripping section. Part of the feed liquid coats the coke particles in the fluidized bed and is subsequently cracked into layers of solid coke and lighter products which evolve as gas or vaporized liquid. Reactor pressure is relatively low in order to favor vaporization of the hydrocarbon vapors which pass upwards from dense phase into dilute phase of the fluid bed in the coking zone and into cyclones at the top of the coking zone where most of the entrained solids are separated from the gas phase by centrifugal force in one or more cyclones and returned to the dense fluidized bed by gravity through the cyclone diplegs. The mixture of steam and hydrocarbon vapors from the reactor is subsequently discharged from the cyclone gas outlets into a scrubber section in a plenum located above the coking zone and separated from it by a partition. It is quenched in the scrubber section by contact with liquid descending over sheds, A pumparound loop circulates condensed liquid to an external cooler and back to the top shed row of the scrubber section to provide cooling for the quench and condensation of the heaviest fraction of the liquid product. This heavy fraction is typically recycled to extinction by feeding back to the coking zone in the reactor.

The coke particles formed in the coking zone pass downwards in the reactor and leave the bottom of the reactor vessel through a stripper section where they are exposed to steam in order to remove occluded hydrocarbons. The solid coke from the reactor, consisting mainly of carbon with lesser amounts of hydrogen, sulfur, nitrogen, and traces of vanadium, nickel, iron, and other elements derived from the feed, passes through the stripper and out of the reactor vessel to a burner or heater where it is partly burned in a fluidized bed with air to raise its temperature from about 480 to 700° C. (about 900° to 1300° F.) to supply the heat required for the endothermic coking reactions, after which a portion of the hot coke particles is recirculated to the fluidized bed reaction zone to transfer the heat to the reactor and to act as nuclei for the coke formation. The balance is withdrawn as coke product.

The FLEXICOKING process is a variant of the fluid coking process that is operated in a unit including a reactor and a heater, but also including a gasifier for gasifying the coke product by reaction with an air/steam mixture to form a low heating value fuel gas. A stream of coke passes from the heater to the gasifier where all but a small fraction of the coke is gasified to a low-Btu gas (~120 Btu/standard cubic feet) by the addition of steam and air in a fluidized bed in an oxygen-deficient environment to form fuel gas comprising carbon monoxide and hydrogen. The fuel gas product from the gasifier, containing entrained coke particles, is returned to the heater to provide most of the heat required for thermal cracking in the reactor with the balance of the reactor heat requirement supplied by combustion in the heater. A small amount of net coke (about 1 percent of feed) is withdrawn from the heater to purge the system of metals and ash. The liquid yield and properties are comparable to those from fluid coking. The fuel gas product (Flexigas), which may contain syngas, is withdrawn from the heater following separation in internal cyclones which return coke particles through their diplegs.

The FLEXICOKING process is described in patents of Exxon Research and Engineering Company, including, for example, U.S. Pat. No. 3,661,543 (Saxton), U.S. Pat. No. 3,759,676 (Lahn), U.S. Pat. No. 3,816,084 (Moser), U.S. Pat. No. 3,702,516 (Luckenbach), U.S. Pat. No. 4,269,696 (Metrailer). A variant is described in U.S. Pat. No. 4,213,848 (Saxton) in which the heat requirement of the reactor coking zone is satisfied by introducing a stream of light hydrocarbons from the product fractionator into the reactor instead of the stream of hot coke particles from the heater. Another variant is described in U.S. Pat. No. 5,472,596 (Kerby) using a stream of light paraffins injected into the hot coke return line to generate olefins. Early work proposed units with a stacked configuration but later units have migrated to a side-by-side arrangement.

FLEXICOKING units useful in the present process may resemble the known type of three-vessel FLEXICOKER and the operating parameters will be similar in many respects.

In particular, the reactor will be operated according to the parameters necessary for the required coking processes. Thus, the heavy oil feed will typically be a heavy (high boiling) reduced petroleum crude; petroleum atmospheric distillation bottoms; petroleum vacuum distillation bottoms, or residuum; pitch; asphalt; bitumen; other heavy hydrocarbon residues; tar sand oil; shale oil; or even a coal slurry or coal liquefaction product such as coal liquefaction bottoms. Such feeds will typically have a Conradson Carbon Residue (ASTM D189-165) of at least 5 wt. %, generally from about 5 to 50 wt. %. Preferably, the feed is a petroleum vacuum residuum.

The heavy oil feed, pre-heated to a temperature at which it is flowable and pumpable, is introduced into the coking reactor towards the top of the reactor vessel through injection nozzles which are constructed to produce a spray of the feed into the bed of fluidized coke particles in the vessel. Temperatures in the coking zone of the reactor are typically in the range of about 450 to 850° C. and pressures are kept at a relatively low level, typically in the range of about 120 to 400 kPag (about 17 to 58 psig), and most usually from about 200 to 350 kPag (about 29 to 51 psig), in order to facilitate fast drying of the coke particles, preventing the formation of sticky, adherent high molecular weight hydrocarbon deposits on the particles which could lead to reactor fouling. The light hydrocarbon products of the coking (thermal cracking) reactions vaporize, mix with the fluidizing steam and pass upwardly through the dense phase of the fluidized bed into a dilute phase zone above the dense fluidized bed of coke particles. This mixture of vaporized hydrocarbon products formed in the coking reactions flows upwardly through the dilute phase with the steam at superficial velocities of about 1 to 2 meters per second (about 3 to 6 feet per second), entraining some fine solid particles of coke which are separated from the cracking vapors in the reactor cyclones as described above. The cracked hydrocarbon vapors pass out of the cyclones into the scrubbing section of the reactor and then to product fractionation and recovery.

As the cracking process proceeds in the reactor, the coke particles pass downwardly through the coking zone, through the stripping zone, where occluded hydrocarbons are stripped off by the ascending current of fluidizing gas (steam). They then exit the coking reactor and pass to the gasification reactor (gasifier) which contains a fluidized bed of solid particles and which operates at a temperature higher than that of the reactor coking zone. In the gasifier, the coke particles are converted by reaction at the elevated temperature with steam and an oxygen-containing gas into a low energy content fuel gas comprising carbon monoxide and hydrogen.

The gasification zone is typically maintained at a high temperature ranging from about 850 to 1000° C. (about 1560 to 1830° F.) and a pressure ranging from about about 0 to 1000 kPag (about 0 to about 150 psig), preferably from about 200 to 400 kPag (about 30 to 60 psig). Steam and an oxygen-containing gas such as air, commercial oxygen or air mixed with oxygen are passed into the gasifier for reaction with the solid particles comprising coke deposited on them in the coking zone. In the gasification zone the reaction between the coke and the steam and the oxygen-containing gas produces a hydrogen and carbon monoxide-containing fuel gas and a partially gasified residual coke product and conditions in the gasifier are selected accordingly. Steam and air rates will depend upon the rate at which cold coke enters from the reactor and to a lesser extent upon the composition of the coke which, in turn will vary according to the composition of the heavy oil feed and the severity of the cracking conditions in the reactor with these being selected according to the feed and the range of liquid products which is required. The fuel gas product from the gasifier may contain entrained coke solids and these are removed by cyclones or other separation techniques in the gasifier section of the unit; cyclones may be internal cyclones in the main gasifier vessel itself or external in a separate, smaller vessel as described below. The fuel gas product is taken out as overhead from the gasifier cyclones. The resulting partly gasified solids are removed from the gasifier and introduced directly into the coking zone of the coking reactor at a level in the dilute phase above the lower dense phase.

Converting Fuel Gas to Gasoline

The fuel gas obtained from the fluidized bed reactor may be upgraded by exposing the fuel gas to an acidic catalyst (such as a zeolite) under effective conversion conditions for olefinic oligomerization, such as in reactor 36. Optionally, the zeolite or other acidic catalyst can also include a hydrogenation functionality, such as a Group VIII metal or other suitable metal that can enhance hydrogenation/dehydrogenation reactions. The olefin-containing feed can be exposed to the acidic catalyst preferably without providing additional hydrogen to the reaction environment. Added hydrogen refers to hydrogen introduced as an input flow to the process, as opposed to any hydrogen that might be generated in-situ during processing. Exposing the fuel gas to an acidic catalyst without providing added hydrogen is defined herein as exposing the feed to the catalyst in the presence of a) less than about 100 SCF/bbl of added hydrogen, or less than about 50 SCF/bbl; b) a partial pressure of less than about 50 psig (350 kPag), or less than about 15 psig (100 kPag) of hydrogen; or c) no hydrogen.

The acidic catalyst used in the processes described herein can be a zeolite-based catalyst, that is, it can comprise an acidic zeolite in combination with a binder or matrix material such as alumina, silica, or silica-alumina, and optionally further in combination with a hydrogenation metal. More generally, the acidic catalyst can correspond to a molecular sieve (such as a zeolite) in combination with a binder, and optionally a hydrogenation metal. Molecular sieves for use in the catalysts can be medium pore size zeolites, such as those having the framework structure of ZSM-5, ZSM-11, ZSM-12, ZSM-22, ZSM-23, ZSM-35, ZSM-48, or MCM-22. Such molecular sieves can have a 10-member ring as the largest ring size in the framework structure. The medium pore size zeolites are a well-recognized class of zeolites and can be characterized as having a Constraint Index of 1 to 12. Constraint Index is determined as described in U.S. Pat. No. 4,016,218 incorporated herein by reference. Catalysts of this type are described in U.S. Pat. Nos. 4,827,069 and 4,992,067 which are incorporated herein by reference and to which reference is made for further details of such catalysts, zeolites and binder or matrix materials.

Additionally or alternately, catalysts based on large pore size framework structures (12-member rings) such as the synthetic faujasites, especially zeolite Y, such as in the form of zeolite USY. Zeolite beta may also be used as the zeolite component. Other materials of acidic functionality which may be used in the catalyst include the materials identified as MCM-36 and MCM-49. Still other materials can include other types of molecular sieves having suitable framework structures, such as silicoaluminophosphates (SAPOs), aluminosilicates having other heteroatoms in the framework structure, such as Ga, Sn, or Zn, or silicoaluminophosphates having other heteroatoms in the framework structure. Mordenite or other solid acid catalysts can also be used as the catalyst.

In various aspects, the exposure of the fuel gas feed to the acidic catalyst can be performed in any convenient manner, such as exposing the fuel gas feed to the acidic catalyst under fluidized bed conditions, moving bed conditions, and/or in a riser reactor. In some aspects, the particle size of the catalyst can be selected in accordance with the fluidization regime which is used in the process. Particle size distribution can be important for maintaining turbulent fluid bed conditions as described in U.S. Pat. No. 4,827,069 and incorporated herein by reference. Suitable particle sizes and distributions for operation of dense fluid bed and transport bed reaction zones are described in U.S. Pat. Nos. 4,827,069 and 4,992,607 both incorporated herein by reference. Particle sizes in both cases will normally be in the range of 10 to 300 microns, typically from 20 to 100 microns.

Acidic zeolite catalysts suitable for use as described herein can be those exhibiting high hydrogen transfer activity and having a zeolite structure of ZSM-5, ZSM-11, ZSM-12, ZSM-22, ZSM-23, ZSM-35, ZSM-48, MCM-22, MCM-36, MCM-49, zeolite Y, and zeolite beta. Such catalysts can be capable of oligomerizing olefins from the fuel gas feed. For example, such catalysts can convert C2-C4 olefins, such as those present in a refinery fuel gas, to C5+ olefins. Such catalysts can also be capable of converting organic sulfur compounds such as mercaptans to hydrogen sulfide without added hydrogen by utilizing hydrogen present in the hydrocarbon feed. Group VIII metals such as nickel may be used as desulfurization promoters. A fluid-bed reactor/regenerator can assist with maintaining catalyst activity in comparison with a fixed-bed system. Further, the hydrogen sulfide produced in accordance with the processes described herein can be removed using conventional amine based absorption processes.

ZSM-5 crystalline structure is readily recognized by its X-ray diffraction pattern, which is described in U.S. Pat. No. 3,702,866. ZSM-11 is disclosed in U.S. Pat. No. 3,709,979, ZSM-12 is disclosed in U.S. Pat. No. 3,832,449, ZSM-22 is disclosed in U.S. Pat. No. 4,810,357, ZSM-23 is disclosed in U.S. Pat. Nos. 4,076,842 and 4,104,151, ZSM-35 is disclosed in U.S. Pat. No. 4,016,245, ZSM-48 is disclosed in U.S. Pat. No. 4,375,573 and MCM-22 is disclosed in U.S. Pat. No. 4,954,325. The U.S. patents identified in this paragraph are incorporated herein by reference.

While suitable zeolites having a coordinated metal oxide to silica molar ratio of 20:1 to 200:1 or higher may be used, it can be advantageous to employ aluminosilicate ZSM-5 having a silica:alumina molar ratio of about 25:1 to 70:1, suitably modified. A typical zeolite catalyst component having Bronsted acid sites can comprises, consist essentially of, or consist of crystalline aluminosilicate having the structure of ZSM-5 zeolite with 5 to 95 wt. % silica, clay and/or alumina binder.

These siliceous zeolites can be employed in their acid forms, ion-exchanged or impregnated with one or more suitable metals, such as Ga, Pd, Zn, Ni, Co, Mo, P, and/or other metals of Periodic Groups III to VIII. The zeolite may include other components, generally one or more metals of group IB, IIB, IIIB, VA, VIA or VIIIA of the Periodic Table (IUPAC).

Useful hydrogenation components can include the noble metals of Group VIIIA, such as platinum, but other noble metals, such as palladium, gold, silver, rhenium or rhodium, may also be used. Base metal hydrogenation components may also be used, such as nickel, cobalt, molybdenum, tungsten, copper or zinc.

The catalyst materials may include two or more catalytic components which components may be present in admixture or combined in a unitary multifunctional solid particle.

In addition to the preferred aluminosilicates, the gallosilicate, ferrosilicate and "silicalite" materials may be employed. ZSM-5 zeolites can be useful in the process because of their regenerability, long life and stability under the extreme conditions of operation. Usually the zeolite crystals have a crystal size from about 0.01 to over 2 microns or more, such as 0.02-1 micron.

In various aspects, the catalyst particles can contain about 25 wt. % to about 40 wt. % H-ZSM-5 zeolite, based on total catalyst weight, contained within a silica-alumina matrix. Typical Alpha values for the catalyst can be about 100 or less. Sulfur conversion to hydrogen sulfide can increase as the alpha value increases.

The Alpha Test is described in U.S. Pat. No. 3,354,078, and in the Journal of Catalysis, Vol. 4, p. 527 (1965); Vol. 6, p. 278 (1966); and Vol. 61, p. 395 (1980), each incorporated herein by reference as to that description.

In various aspects, the fuel gas feed may be exposed to the acidic catalyst by using a moving or fluid catalyst bed reactor. In such aspects, the catalyst may be regenerated, such via continuous oxidative regeneration. The extent of coke loading on the catalyst can then be continuously controlled by varying the severity and/or the frequency of regeneration. In a turbulent fluidized catalyst bed the conversion reactions are conducted in a vertical reactor column by passing hot reactant vapor upwardly through the reaction zone and/or reaction vessel at a velocity greater than dense bed transition velocity and less than transport velocity for the average catalyst particle. A continuous process is operated by withdrawing a portion of coked catalyst from the reaction zone and/or reaction vessel, oxidatively regenerating the withdrawn catalyst and returning regenerated catalyst to the reaction zone at a rate to control catalyst activity and reaction severity to affect feedstock conversion. Preferred fluid bed reactor systems are described in Avidan et al U.S. Pat. No. 4,547,616; Harandi & Owen U.S. Pat. No. 4,751,338; and in Tabak et al U.S. Pat. No. 4,579,999, incorporated herein by reference. In other aspects, other types of reactors can be used, such as fixed bed reactors, riser reactors, fluid bed reactors, and/or moving bed reactors.

In one or more aspects, effective conversion conditions for exposing the fuel gas feed to an acidic catalyst can include a temperature of about 300° F. (149° C.) to about 900° F. (482° C.), or about 350° F. (177° C.) to about 850° F. (454° C.), or about 350° F. (177° C.) to about 800° F. (427° C.), or about 350° F. (177° C.) to about 750° F. (399° C.), or about 350° F. (177° C.) to about 700° F. (371° C.), or a temperature of at least about 400° F. (204° C.), or at least about 500° F. (260° C.), or at least about 550° F. (288° C.), or at least about 600° F. (316° C.); a pressure of about 50 psig (0.34 MPag) to about 1100 psig (7.6 MPag), or a pressure of about 100 psig (0.69 MPag) to about 1000 psig (6.9 MPag), or a pressure of about 100 psig (0.69 MPag) to about 200 psig (1.4 MPag), or about 150 psig (1.0 MPag) to about 975 psig (6.7 MPag), or about 200 psig (1.4 MPag) to about 950 psig (6.6 MPag), or about 250 psig (1.7 MPag) to about 900 psig (6.2 MPag), or about 300 psig (4.1 MPag) to about 850 psig (5.9 MPag), or about 300 psig (4.1 MPag) to about 800 psig (5.5 MPag), or a pressure of at least about 50 psig (0.34 MPag), or a pressure of at least about 100 psig (0.69 MPag), or a pressure of at least about 150 psig (1.0 MPag), or a pressure of at least about 200 psig (1.4 MPag), or a pressure of at least about 250 psig (1.7 MPag), or a pressure of at least about 300 psig (4.1 MPag), or a pressure of at least about 350 psig (2.4 MPag); and a total feed WHSV of about 0.05 hr-1 to about 40 hr-1, or about 0.05 to about 30 hr-1, or about 0.1 to about 20 hr-1, or about 0.1 to about 10 hr-1. Optionally, the total feed WHSV can be about 1 hr-1 to about 40 hr-1 to improve C5+ yield.

In addition to a total feed WHSV, a WHSV can also be specified for just the olefin compounds in the feed. In other words, an olefin WHSV represents a space velocity defined by just the weight of olefins in a feed relative to the weight of catalyst. In one or more aspects, the effective conversion conditions can include an olefin WHSV of at least about 0.8 hr-1, or at least about 1.0 hr-1, or at least about 2.0 hr-1, or at least about 3.0 hr-1, or at least about 4.0 hr-1, or at least about 5.0 hr-1, or at least about 8.0 hr-1, or at least about 10 hr-1, or at least about 15 hr-1. In the same or alternative aspects, the effective conversion conditions can include an olefin WHSV of about 40 hr-1 or less, or about 30 hr-1 or less, or about 20 hr-1 or less. In certain aspects, the effective conversion conditions can include an olefin WHSV of about 0.2 hr-1 to about 30 hr-1, or about 0.8 hr-1 to about 20 hr-1, or about 0.8 hr-1 to about 15 hr-1, or about 0.8 hr-1 to about 10 hr-1, or about 0.8 hr-1 to about 7 hr-1, or about 0.8 hr-1 to about 5 hr-1, or about 1.0 hr-1 to about 30 hr-1, or about 1.0 hr-1 to about 20 hr-1, or about 1.0 hr-1 to about 15 hr-1, or about 1.0 hr-1 to about 10 hr-1, or about 1.0 hr-1 to about 7 hr-1, or about 1.0 hr-1 to about 5 hr-1, or about 2.0 hr-1 to about 30 hr-1, or about 2.0 hr-1 to about 20 hr-1, or about 2.0 hr-1 to about 15 hr-1, or about 2.0 hr-1 to about 10 hr-1, or about 2.0 hr-1 to about 7 hr-1, or about 2.0 hr-1 to about 5 hr-1, about 4.0 hr-1 to about 30 hr-1, or about 4.0 hr-1 to about 20 hr-1, or about 4.0 hr-1 to about 15 hr-1, or about 4.0 hr-1 to about 10 hr-1, or about 4.0 hr-1 to about 7 hr-1. An olefin WHSV of about 1 hr-1 to about 40 hr-1 can be beneficial for increasing the C5+ yield.

In various aspects, decreasing the temperature when the olefin WHSV is increased, e.g., when the olefin WHSV is increased above 1 hr-1, may improve product yield. For example, in such aspects, temperatures of about 600° F. (316° C.) to about 800° F. (427° C.), or about 650° F. (343° C.) to about 750° F. (399° C.) may aid in increasing product yield, such as the yield of C5+ compounds, when the olefin WHSV is increased above 1 hr-1.

Converting Syngas to Gasoline Via Methanol Intermediate

FLEXIGAS fuel gas obtained from the FLEXICOKING unit may be fed to a separation block to produce a syngas feed, which may be converted to gasoline by conversion to a methanol intermediate. The chemistry of methanol synthesis from normal syngas may be characterized by the following equations (1) and (2):

$$CO_2 + 3H_2 = CH_3OH + H_2O \quad (1)$$

$$CO + H_2O = CO_2 + H_2 \quad (2)$$

The water that is produced in situ in the catalyst by reaction (1) reacts rapidly with the carbon monoxide present in the syngas feed, resulting in formation of carbon dioxide and hydrogen, both of which are reactants for the main synthesis reaction (1). As a result, the water produced in situ does not accumulate in the catalyst and does not adversely affect the thermodynamic equilibrium considerations. However, the production of methanol does adversely affect the thermodynamics of reactions (1) and (2).

When the products of methanol synthesis reaction are contacted with a dehydration catalyst, such as γ-alumina, the additional reaction takes place:

$$2CH_3OH = CH_3OCH_3 + H_2O \quad (3)$$

By reaction (3), more methanol is consumed and water is generated along with dimethyl ether. The dehydration catalyst may be in the same reactor as the methanol synthesis catalyst for in situ dehydration or it may be in a separate downstream reactor.

The catalysts comprising the catalysts for converting the syngas to methanol may be those known in the art which usually comprise copper, zinc oxide and alumina, zirconia and/or titania supports. Such catalysts are disclosed, for example, in U.S. Pat. No. 4,417,000. A particularly preferred catalyst comprises copper (measured as the metal) ranging from about 25% to about 65% by weight, basis total catalyst, more preferably ranging from about 35% to 55% by weight. The zinc oxide (as measured by the metal oxide) will range from about 35% by weight to about 65% by weight of the total catalyst, and preferably from about 40% by weight to 50% by weight. The support will usually be an alumina support but may also be titania or zirconia.

If employed, the catalyst which may be used to convert the methanol to dimethyl ether may be a dehydration catalyst such as γ-alumina, zeolite, or aluminum silicate. The weight ratio of the methanol-producing catalyst to the dimethyl ether-producing catalyst in the slurry will be about 100 to 1, more preferably from 50 to 1.

The catalysts may be intimately admixed together in a single bed or may be in two successive beds (e.g., as depicted in the FIGURE as reactors 48 and 52) or in a series of alternating layers. The reaction zone(s) for producing methanol and dimethyl ether may be operated as a fixed or fluidized bed with upflow or downflow of reactants and conventional product removal. Typically, the reaction product from the synthesis of methanol and dehydration of methanol to dimethyl ether will comprise dimethyl ether as a major component. Some water (some in the form of steam) and some unreacted carbon monoxide hydrogen and carbon dioxide appeared. A small amount of methanol may also be present.

The organic intermediates comprising essentially dimethyl ether formed in the dimethyl ether reactor may then be fed into a subsequent hydrocarbon conversion stage, preferably with a minimum of interstage cooling. In the subsequent stage the catalysts are zeolites which are useful for converting hydrocarbons to gasoline, which is a fuel comprising liquid hydrocarbons in the range of C5 to about 400° F. boiling point. These zeolite catalysts which are referred may be those disclosed in U.S. Pat. No. 3,894,102 and in particular are zeolite catalysts having a silica to alumina ratio of at least 12 and preferably higher ratios to at least about 60. The disclosure of U.S. Pat. No. 3,894,102 is incorporated by reference herein in its entirety.

The zeolites, when prepared in the presence of organic cations, are catalytically inactive but may be activated by heating in an inert atmosphere, preferably at 1000° F. for 1 hour followed by a base exchange with ammonium salts and calcination at 1000° F. in air. More generally, it is desirable to activate this type of zeolite catalyst by base exchange with ammonium salts followed by calcination in air at about 1000° F. for from about 15 minutes to 24 hours.

The intermediate product comprising dimethyl ether as a major product may then be converted to a hydrocarbon product, typically comprising liquid hydrocarbons boiling at C5 to about 450° F. range, by contacting the dimethyl ether with the zeolite catalysts at a temperature in the range of 650° to 1000° F. (e.g., in reactor 56 of the FIGURE). Typical space velocities (calculated on dimethyl ether) of contact are from 0.1 to 50 kg DME/kg cat/hr.

For example, the zeolite for converting dimethyl ether to a hydrocarbon product may be selected from a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The preferred class of catalysts is characterized by a Constraint Index of 1 to 12 and a silica:alumina ratio of at least 12:1 and preferably higher e.g., 20:1 to 70:1, or even higher. Constraint Index of a zeolite is a convenient measure of the extent to which a zeolite provides constrained access to its internal structure for molecules of different sizes. It is therefore, a characteristic of the structure of the zeolite but is measured by a test which relies upon the possession of cracking activity by the zeolite. The sample of zeolite selected for determination of the Constraint Index of a zeolite should therefore represent the structure of the zeolite (manifested by its X-ray diffraction pattern) and have adequate cracking activity for the Index to be determined. If the cracking activity of the selected zeolite is too low, the Constraint Index may be determined by using a zeolite sample of the same structure but higher cracking activity which may be obtained, for example, by using an aluminosilicate zeolite of higher aluminum content. Details of the method of determining Constraint Index and of the values of the Index for typical zeolies are given in U.S. Pat. No. 4,016,218 to which reference is made for such details and other information in this respect.

Preferred zeolites which have the specified values of Constraint Index and silica:alumina ratio include zeolites having a ZSM-5 structure such as ZSM-5, ZSM-11, ZSM-12, ZSM-35, ZSM-38 and ZSM-48, which are described in U.S. Pat. No. 3,702,886 (ZSM-5), U.S. Pat. No. 3,709,979 (ZSM-11), U.S. Pat. No. 3,832,449 (ZSM-12), U.S. Pat. No. 4,076,842 (ZSM-23) and U.S. Pat. No. 4,016,245 (ZSM-35), U.S. Pat. No. 4,046,859 (ZSM-38) and U.S. Pat. No. 4,397,827 (ZSM-48), and reference is made to these patents for details of these zeolites, their preparation and properties. Of these zeolites, ZSM-5 is preferred.

The zeolite catalyst used is at least partly in the hydrogen form e.g., HZSM-5; but other cations, e.g., Periodic Groups III-VIII or rare earth cations may also be present. When the zeolites are prepared in the presence of organic cations they may be quite inactive possibly because the intracrystalline free space is occupied by the organic cations from the forming solution. The zeolite may be activated by heating in an inert atmosphere to remove the organic cations e.g., by heating at over 500° C. for 1 hour or more. The hydrogen form can then be obtained by base exchange with ammonium salts followed by calcination e.g. at 500° C. in air. Other cations e.g., metal cations can be introduced by conventional base exchange techniques.

The hydrocarbon product converted from dimethyl ether may then be further upgraded by oligomerization and/or dehydration. For example, it may be upgrade using the same catalyst and similar conversion conditions that are used to convert the fuel gas obtained from the fluidized bed reactor to gasoline, e.g., the hydrocarbon product may be contacted with an acidic catalyst (such as a zeolite) under effective conversion conditions for olefinic oligomerization. Optionally, the zeolite or other acidic catalyst can also include a hydrogenation functionality, such as a Group VIII metal or other suitable metal that can activate hydrogenation/dehydrogenation reactions. The olefin-containing product can be exposed to the acidic catalyst without providing substantial additional hydrogen to the reaction environment.

Converting Fuel Gas and Methanol to Gasoline in Common Reactor

In a preferred embodiment, reactor 52 and 56 may be omitted in the system illustrated in the FIGURE, and the methanol intermediate may be fed to reactor 36 with fuel gas 16 for combined upgrading. The combined reaction is faster and allows usage of less reactor volume and/or catalyst activity. In such a configuration, the common reactor may employ the same catalyst and operate under the same reaction conditions as described herein for "Converting Fuel Gas to Gasoline."

EXAMPLE

A 64,000 BPD fluidized bed FLEXICOKING reactor with integrated heater and gasifier receiving a heavy oil feed of 4.4 API gravity, may be capable of producing the standard product slate illustrated in Table 1.

TABLE 1

| | |
|---|---|
| Total C3— | 95.5 klb/hr |
| Total C4 | 24.8 klb/hr |
| Naphtha C5/430 F | 172.2 klb/hr |
| Gas Oil 430/650 F | 113.8 klb/hr |
| Gas Oil 650/950 F | 160.7 klb/hr |

TABLE 1-continued

| Gross Coke | 299.1 | klb/hr |
|---|---|---|
| H$_2$S + contaminants | 10 | klb/hr |
| TOTAL | 972 | klb/hr |

TABLE 2

| FLEXIGAS from heater | 1583.8 | klb/hr |
|---|---|---|
| Methanol intermediate | 18,518 | lbmol/hr |
| Gasoline from methanol intermediate | 19,702 | Bbl/day |
| Excess H2 need | 283 | MMSCFD |
| Fuel gas from fluidized reactor | 30.4 | klb/hr |
| Gasoline from fuel gas | 1,642 | Bbl/day |
| Total (Bbl/day) | 21,344 | Bbl/day |
| TOTAL | 237 | klb/hr |

The invention claimed is:

1. A method of making gasoline comprising:
   converting a resid-containing feed to a first fuel gas and a fluid coke in a fluidized bed reactor,
   gasifying the fluid coke with steam and air to produce a second fuel gas, said second fuel gas comprising a syngas;
   contacting the first fuel gas with a first conversion catalyst under first effective conversion conditions in a reaction zone to form an effluent comprising C$_5$+ hydrocarbon compounds, wherein the first effective conversion conditions comprise a pressure of less than about 300 psig (2.1 MPa) and a temperature of at least about 550° F. (288° C.);
   converting at least a portion of the syngas to a methanol intermediate product;
   converting the methanol intermediate product to gasoline boiling range hydrocarbons by contacting the methanol intermediate product with the first conversion catalyst under the first effective conversion conditions in the reaction zone;
   separating the effluent comprising the C$_5$+ hydrocarbon compounds and the gasoline boiling range hydrocarbons in a deethanizer and a stabilizer to form a deethanized, stabilized effluent; and
   blending the deethanized, stabilized effluent with one or more other gasoline streams.

2. The method of claim 1, wherein the resid-containing feed comprises atmospheric distillation resid, vacuum resid, catalytic cracker residual oil, hydrocracker residual oils, or a combination thereof.

3. The method of claim 1, wherein the resid-containing feed is thermally decomposed in the fluidized bed reactor at a temperature between about 480 to 590° C. (about 900 to 1100° F.).

4. The method of claim 1, wherein the first conversion catalyst is an acidic catalyst.

5. The method of claim 4, wherein the first conversion catalyst is ZSM-5.

6. The method of claim 4, wherein the first fuel gas is exposed to the acidic catalyst without providing added hydrogen.

7. A method of making gasoline comprising:
   converting a resid-containing feed to a first fuel gas and a fluid coke in a fluidized bed reactor,
   gasifying the fluid coke with steam and air to produce a second fuel gas, said second fuel gas comprising a syngas;
   contacting the first fuel gas with a first conversion catalyst under first effective conversion conditions in a reaction zone to form an effluent comprising C$_5$+ hydrocarbon compounds, wherein the first effective conversion conditions comprise a pressure of less than about 300 psig (2.1 MPa) and a temperature of at least about 550° F. (288° C.);
   converting at least a portion of the syngas to a methanol intermediate product, a dimethyl ether intermediate product, or a combination thereof;
   converting the methanol intermediate product, the dimethyl ether intermediate product, or the combination thereof to gasoline boiling range hydrocarbons by contacting the methanol intermediate product with the first conversion catalyst under the first effective conversion conditions in the reaction zone;
   separating the effluent comprising the C$_5$+ hydrocarbon compounds and the gasoline boiling range hydrocarbons in a deethanizer and a stabilizer to form a deethanized, stabilized effluent; and
   blending the deethanized, stabilized effluent with one or more other gasoline streams.

8. The method of claim 7, wherein the resid-containing feed comprises atmospheric distillation resid, vacuum resid, catalytic cracker residual oil, hydrocracker residual oils, or a combination thereof.

9. The method of claim 7, wherein the resid-containing feed is thermally decomposed in the fluidized bed reactor at a temperature between about 480 to 590° C. (about 900 to 1100° F.).

10. The method of claim 7, wherein the first conversion catalyst is an acidic catalyst.

11. The method of claim 10, wherein the first conversion catalyst is ZSM-5.

12. The method of claim 10, wherein the first fuel gas is exposed to the acidic catalyst without providing added hydrogen.

* * * * *